United States Patent [19]

Knifton et al.

[11] Patent Number: 5,344,984
[45] Date of Patent: Sep. 6, 1994

[54] METHOD FOR PREPARING "TWIN-TAILED" POLYOXYALKYLENE TERTIARY AMINES

[75] Inventors: John F. Knifton; Carter G. Naylor, both of Austin, Tex.

[73] Assignee: Texaco Chemical Company, White Plains, N.Y.

[21] Appl. No.: 45,284

[22] Filed: Apr. 8, 1993

Related U.S. Application Data

[63] Continuation-in-part of Ser. No. 469,865, Jan. 24, 1990, abandoned.

[51] Int. Cl.$^5$ .................................. C07C 209/14
[52] U.S. Cl. ...................... 564/399; 564/347; 564/348; 564/353; 564/402; 564/474; 564/480; 564/505
[58] Field of Search ............... 564/348, 402, 474, 480, 564/505, 399, 347, 353

[56] References Cited

U.S. PATENT DOCUMENTS 4,650,865  3/1987  Lange et al. ..................... 564/505
5,003,107  3/1991  Zimmerman et al. ............ 564/480

FOREIGN PATENT DOCUMENTS 1225102  8/1987  Canada .

OTHER PUBLICATIONS

Barfknecht et al., *Chemical Abstracts*, 84:25771z (1975).
Esaki et al., *Chemical Abstracts*, 77:140956f (1972).
Horvath et al., *Chemical Abstracts*, 110:95345f (1989).
Kunitomo et al., *Chemical Abstracts*, 77:14948s (1972).
Telepova et al., *Chemical Abstracts*, 75:78126p (1971).
Yanagida et al., *Chemical Abstracts*, 98:197566s (1983).
Nippon Oils and Fats Co., Ltd., *Chemical Abstracts*, 102:223243g (1985).
Reetz, *Chemical Abstracts*, 52:15565i (1958).
Sayigh et al., *J. Chem. Soc.*, 1963, pp. 3144–3146.
Shimizu et al., *Chemical Abstracts*, 109:192637b (1988).

*Primary Examiner*—Glennon H. Hollrah
*Assistant Examiner*—Scott C. Rand
*Attorney, Agent, or Firm*—Russell R. Stolle; Cynthia L. Kendrick

[57] ABSTRACT

A method for preparing "twin-tailed" tertiary amines which have two moles of alkoxylated phenol bonded to each nitrogen function of a molecule of methylamine and represented by the formula:

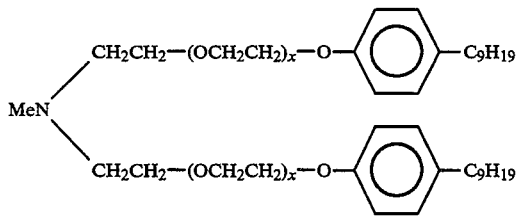

wherein x represents zero to about 30 which comprises alkylating a mole of methylamine with two moles of alkoxylated alkylphenol over a catalyst comprising:
  5 to 70% nickel;
  1 to 20% copper;
  0.1 to 10% chromium; and
  0.1 to 10% molybdenum on an alumina support.

2 Claims, No Drawings

METHOD FOR PREPARING "TWIN-TAILED" POLYOXYALKYLENE TERTIARY AMINES

This is a continuation-in-part of Ser. No. 07/469,865, filed Jan. 24, 1990, now abandoned.

FIELD OF THE INVENTION

This invention relates to tertiary amines. More particularly, this invention relates to the preparation of polyoxyalkylene tertiary amines synthesized from methylamine and an alkoxylated alkylphenol or alcohol. This invention describes the preparation of "twin-tailed" polyoxyalkylene tertiary amine having two moles of alkoxylated alkylphenol or alcohol bonded to each tertiary nitrogen function.

This composition of matter has good surface active properties.

BACKGROUND OF THE INVENTION

Aliphatic tertiary amines are important industrial intermediates for preparing corrosion inhibitors, fungicides, dye adjuvants and softening agents for fabrics, etc. and there are a number of methods known for their preparation.

N,N-dimethylalkylamides can be reduced commercially to tertiary amines at high temperature and pressure in the presence of Cu—Cr catalysts. See S. H. Shapiro in E. S. Pattison, ed., *Fatty Acids and Their Industrial Applications*, Marcel Dekker, Inc. New York, 1968, p. 124.

The catalytic amination of aliphatic alcohols is likely the most economic and simplest route to tertiary amines. In a recent article by Abe et al. in Applied Catalysis, 52, 171 (1989) is described the production of N,N-dimethyldodecylamine from dodecyl alcohol and dimethylamine using copper stearate and nickel stearate, although the likely active catalysts are colloidal copper and nickel. This article also reviews earlier catalyst studies on this route to aliphatic tertiary amines, including the use of Cu—Re, Raney nickel and supported Cu—Sn—Na catalysts.

A catalyst of Cu—Cr—Ba has been used in alkylation of long-chain amines with short-chain alcohols to yield tertiary amines. See Brit. Pat. 675,852 (Jan. 16, 1957) (to Armour & Co.) and Jpn. Kokai 74 82,605 (Aug. 8, 1974) and 74 81,306 (Aug. 6, 1974).

U.S. Pat. No. 3,223,734 teaches the alkylation of long-chain amines to high molecular weight tertiary amines by treating the amine with a long-chain alcohol in the presence of Raney nickel or Cu—Cr catalyst.

A method has been disclosed for producing tertiary amines wherein a dodecyl alcohol and dimethyl amine are reacted in the presence of a suspended copper chromium catalyst. See 19 Japan Patent Agency (JP) 12 Kokai Patent Gazette (A), 11 Publication No: 59-222 448 [84-222448] 43 Publication Date: Dec. 14, 1984.

In an article titled "Recent Trends of Catalysts for Production of Aliphatic Tertiary Amines", Okabe Kazuhiko and Abe Hiroshi (Wakayama First Res. Lab., Kao Corp. Wakayama, Japan) *Yukagaku*, 1988, 37(7), 485-91 (Japan), there is a review of catalysts which are suitable for amination of alkanols, with the authors having researched and developed the performance of copper-nickel amination catalysts in particular.

Tallow alcohol has been reacted with dimethylamine vapor over a catalyst comprising copper carbonate and nickel carbonate to produce dimethylalkylamine. See U.S. Pat. No. 4,683,336.

In *Soap/Cosmetics/Chemical Specialties*, Febuary 1985, p. 54, there is discussed a technological breakthrough in amine chemical manufacture by Onyx Chemical Company wherein detergent range fatty alcohols are catalytically reacted directly with diethylamine, by-passing the traditional hydrochlorination step, thus allowing for a cleaner, easier to control tertiary amine with very precise alkyl radical distribution.

European Patent Application No. 0 239 934 demonstrates the selective production of mono-aminated products from the amination of ethylene glycol or 1,3-propanediol with a secondary amine which is effected in the presence of a ruthenium compound.

In PCT Int. Appl. WO 88 06,579 (Cl. CO7C93/04), Sep. 7, 1988, there is disclosed the amination of alkoxylated alcohols with secondary amines in the presence of a catalyst comprising a mixture of CuO or Cu(OH)$_2$.

Other art involving the preparation of tertiary amines describes catalysts containing copper, alkaline earth metals, copper chromite, Cu—Ni—Ru, Cu—Sn, Cu—Cr, Cu—Zn/Al$_2$O$_3$, Pd—C and Pt group metals. Generally the reactants include alcohols and primary or secondary amines.

See for example:
U.S. Pat. No. 3,128,311
U.S. Pat. No. 4,625,063
U.S. Pat. No. 4,625,064
E.P. 233,317
Ger. Offen. DE 3,246,978
Ger. Offen. DE 3,523,074
Ger. Offen. DE 3,432,015-A
J. P. 59,106,441
J. P. 59,222,448
J. P. 62,149,646
J. P. 62,149,647
CN 85,100,326

The principal uses of dialkylamines and trialkylamines are discussed in an article titled "Cationic Surfactants", *Stanford Research Institute*, December (1985), p. 8. The majority of the dialkylamines produced via fatty nitrile chemistry are subsequently converted to quaternary ammonium salts.

From a survey of the available art it appears the source of the alcohol reacted with an amine is often from naturally-occurring raw materials such as coconut oil, tallow and tall oil.

There is a comparison of the cost of production of C$_{12}$ dimethyl fatty amines by the synthetic petrochemical route using, for example, Ziegler alcohols, compared with similar tertiary nitrogen chemicals derived from naturally occurring raw materials such as coconut oil, tallow or tall oil in Chem Systems, *Process Evaluation/Research Planning*, Report No. 85-6 (September '86) at Sec. 1.3000.

For the most part, the art referred to focuses on the synthesis of N,N-dimethylalkylamines by reaction of dimethylamine or monomethylamine with a long chain alcohol, e.g. tallow alcohol or dodecyl alcohol. It would be an important advance in the art to have a process for the selective production of "twin tailed" N-methyldialkylamines, particularly "twin-tailed" N-methyldi(polyoxyalkylene)tertiary amines, that could be produced from readily available reactants in yields which are improvements over yields for related tertiary amines.

SUMMARY OF THE INVENTION

It is an object of the present invention to provide a method of selectively preparing a novel "twin-tailed" tertiary amine using reactants which are readily available. More specifically, in accordance with the present invention, there is provided a process for the preparation of N-methyldi(polyoxyalkylene)tertiary amines which comprises reacting methylamine and an ethoxylated alkylphenol or alcohol at a temperature of about 180° C. to 240° C. and a pressure of about 1000 psi to about 3000 psi.

DESCRIPTION OF THE PREFERRED EMBODIMENT

According to the present invention a novel tertiary amine with "twin-tails" can be prepared having two moles of alkoxylated alkylphenol bonded to each tertiary nitrogen function. The novel tertiary amines are prepared by alkylation of methylamine by two moles of an ethoxylated alkylphenol over a catalyst comprising a nickel bulk catalyst consisting essentially of 5 to 70% nickel, 1 to 20% copper, 0.1 to 10% chromium and 0.1 to 10% to molybdenum on an alumina support. The alkylation takes place at elevated temperatures and pressures. The products are in liquid form and are useful as surface active agents. Those skilled in the art will see the desirability of the symmetrical structure of the instant tertiary amine.

The novel tertiary amines of the present invention are amines which contain as the principle reaction components methylamine and an ethoxylated alkylphenol or alcohol. The novel "twin-tailed" tertiary amines were prepared by the reaction (Eq. 1) of methylamine and ethoxylated alkylphenol or alcohol according to the following:

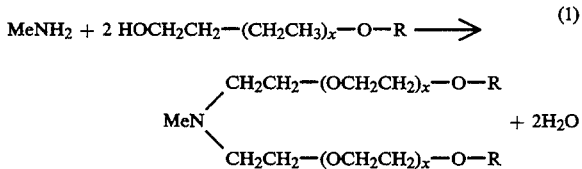

where R is an alkyl or alkylphenyl containing from 4 to 20 carbons, and where x has a value of from one to about 30.

In addition to methylamine, the preferred starting materials include ethoxylated nonylphenols which can be represented by the formula:

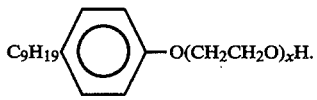

and ethoxylated alcohols having the formula

where n from about 4 to 20 and x has the same value as given above.

Materials having this formula are available from Texaco Chemical Company, as well as other suppliers, under the tradename SURFONIC® N-series.

It has surprisingly been discovered that the SURFONIC® N ethoxylated nonylphenol products appear to be very well suited for reacting with methylamine under the conditions of this invention as evidenced by the good results obtained with SURFONIC® N-95 (containing 9.5 oxethylene groups) in Examples I through IX.

In the method of this invention a solvent was not necessary. The reactor was charged with the catalyst and then a mixture of the nonylphenol ethoxylate and methylamine was fed separately to the reactor at a fixed ratio.

A variety of aliphatic primary amines may be reacted with the alkylphenol ethoxylate in the desired synthesis of Eq. 1. Suitable primary amines include those containing 1 to 6 carbon atoms per molecule, such as monomethylamine, monoethylamine, n-propylamine and n-hexylamine. Primary amines with branched-chain alkyl groups, such as isopropylamine, are less satisfactory. Monomethylamine is the preferred coreactant.

The preferred catalyst useful in the method of this invention comprises nickel in combination with copper, chromium and molybdenum. The transition metals can be chosen from a wide variety of organic or inorganic compounds, complexes, etc. It is only necessary that the catalyst precursor actually employed contain said metal in any of its ionic states. The actual catalytically active species may then comprise, for example copper, nickel or chromium or a combination thereof. Preferably, said catalyst will also contain molybdenum.

The copper-catalyst precursor may take many different forms. For instance the copper may be added to the catalyst precursor mix in an oxide, salt or complex form. For example, the copper may be introduced as cupric oxide, cuprous oxide, copper nitrate, copper sulfate, copper chloride, copper acetate and copper phosphate. Alternatively, the copper may be added as a complex derivative, such as copper(II) 2,4-pentanedionate, copper(II) gluconate and copper methoxide.

The nickel-catalyst precursor may also take many different forms. For instance the nickel may be added to the catalyst formulation in an oxide, salt or complex form. For example the nickel may be introduced as nickel oxide, nickel nitrate, nickel sulfate, nickel chloride and nickel acetate. Alternatively, the nickel may be added as a complex derivative such as nickel 2-ethylhexanoate, nickel(II) 2,4-pentanedionate and nickel glycinate.

The chromium-catalyst precursor may also take several different forms, but preferably it is added as the chromite or chromate ions. Particularly preferable is the addition of chromium as the chromite moiety in copper chromite. Chromium may also be added in an oxide, salt or complex form, such as for example, chromium nitrate, chromium(III) acetate, chromium(III) chloride and chromium phosphate, as well as sodium chromate. The preferred transition metals in addition to nickel are copper, chromium and molybdenum.

Moderate yields can be obtained where a copper-based compound is used as the catalyst, as in the case of copper chromite, which is represented in Example II. In this case a promoter from the alkaline earth group is desirable. It has been surprisingly discovered in this invention that best results were observed where the Ni—Cu—Cr catalyst was deposited on a support.

The support should preferably comprise one or more elements from Group III or Group IV of the periodic table. Said elements should preferably be in an oxide form, and may include aluminum, silicon, titanium and zirconium. Suitable oxide supports include alumina, silica, titania and zirconia. Good results have been achieved where the support is alumina.

Where nickel is used with copper and chromium, the quantities employed in said catalyst may vary. Typically, the nickel content may be varied from 5 to ca. 70%, basis the total weight of the catalyst. The preferred amount of nickel is 10 to 50%. Copper and chromium are then present in lesser amounts. The preferred amount of copper is 1 to 20%. The preferred amount of chromium is 0.1 to 10% and molybdenum is preferably present in an amount of 0.1 to 10%. A catalyst which contains nickel, copper and chromium on a support, and comprises 41 wt % nickel, 6.4 wt % copper and 1.2 wt % chromium and 2 wt % molybdenum is Harshaw Ni-2728, E 1/32" extrudates.

The temperature range which can usefully be employed is variable depending upon other experimental factors, including the pressure and the choice of particular species of catalyst among other things. The range of operability is from about 150° C. to about 300° C. A narrow range of 180° C. to 240° C. is preferred. A suitable pressure range is from about 100 psi to 5000 psi, the preferred range is from 1500 psi to 3000 psi. Good results were obtained with a pressure of about 2000 psi.

The "twin-tailed" amine products were identified by chromatography (gpc) and with wet chemical techniques. Analyses have, for the most part been by parts in weight; all temperatures are in degrees centigrade and all pressures are in pounds per square inch gauge (psig). The selectivity means the moles of novel "twin-tailed" tertiary amine divided by the moles of reactant.

The invention can be illustrated by the following Examples which are not to be considered limitative.

The data in the accompanying Examples illustrate:
1. The synthesis of the desired twin-tailed tertiary amine from SURFONIC ® N-95 and methylamine over a Ni—Cu—Cr—Mb-on-alumina catalyst (Harshaw Ni-2728, 1/32" extrudate), with high SURFONIC ® N-95 conversion and no detected cracking to light products (see Example I).
2. A similar synthesis using a barium-promoted (9-10%) copper chromite catalyst (Harshaw Cu-1184, T ⅛") (see Example II).
3. The preparation of tertiary amine from SURFONIC ® N-95 plus dimethylamine using Ni-2728 (Example III).
4. A rerun of the composite product from Example I through the same Ni-2728 catalyst to achieve improved levels of desired, twin-tailed tertiary amine, as well as improved SURFONIC ® N-95 conversion (Example IV).
5. Improved yields of desired tertiary amines by operating with Ni-2728 at lower feed rates (Example V).
6. The synthesis of twin-tailed tertiary amine from SURFONIC ® N-40 (containing four oxyethylene groups) plus methylamine (Example IX).
7. Typical surfactant data for the twin-tailed tertiary amine products of Examples I and IV, with lower cloud points and higher viscosities for the rerun product (see Examples VI and VII).
8. Comparative runs showing essentially no formation of desired tertiary amine with the Ni—Cu—Cr bulk metal catalyst, Ni-2715, and very little tertiary amine with isopropylamine as the coreactant (Comparative Examples A & B).

EXAMPLE I

To a 550-cc tubular, plug-flow reactor fitted with heating, cooling and pressure control was charged a nickel, copper and chromium on alumina catalyst containing about 40% nickel (Harshaw/Filtrol Ni-2728 E 1/32"). A mixture of SURFONIC ® N-95 nonylphenol ethoxylate and methylamine were fed separately to the reactor at ratio of 0.22 and 0.02 lb/hr respectively, first under a stream of nitrogen, then a mix of nitrogen and hydrogen, and finally pure hydrogen. Under steady state conditions the hydrogen flow rate was 16 l/hr, the back pressure 2000 psi. The product liquid was collected overnight, stripped of unreacted methylamine plus lights, and analyzed by chromatography (gpc) and wet chemical techniques.

A series of products were likewise recovered at five different operating temperatures. The results for duplicate samples are summarized in Table I.

The data indicate that at the operating temperature range of 200 °–210° C.:
a. The significant product fraction was the desired "twin-tailed" tertiary amine (see high tertiary amine content in Col. 4), but higher amounts of non-primary amine assumed to be "single-tailed" amines, were produced (Col. 5).
b. Conversion of SURFONIC ® N-95 was high (unreacted OH is low in Col. 6).
c. There was no detected cracking to light by-products (see gpc data, Col. 9).

COMPARATIVE EXAMPLE A

Following the procedures of Example 1, the 550-cc tubular reactor was charged with a nickel, copper and chromium bulk metal catalyst containing about 68% nickel (Harshaw/Filtrol Ni-2715, T ⅛"). The catalyst was employed without an alumina support. A mixture of SURFONIC ® N-95 and methylamine were fed separately to the reactor at the rate of 0.22 and 0.02 lb/hr, respectively. The hydrogen flow rate was again 16 l/hr, the pressure 2000 psi. The product liquids were collected in duplicate at each reactor temperature, stripped of unreacted methylamines and lights, and analyzed by chromatography and wet chemical techniques. The results are summarized in Table II.

The data indicate that Ni-2715 catalyst gave poor yields of desired "twin-tailed" tertiary amines under these conditions (low tertiary amine content, Col. 4). Furthermore, there was considerable cracking to light products (see gpc data, Col. 9). Comparative Example A demonstrates inferior results using a nickel, copper and chromium catalyst with no alumina support.

COMPARATIVE EXAMPLE B

Following the procedures of Example I, the 550-cc tubular reactor was again filled with the nickel, copper and chromium-on-alumina catalyst (Ni-2728 E 1/32"), but this time the liquid comprised SURFONIC ® N-95 and isopropylamine. Here the feed rates were 0.22 and 0.04 lb/hr, respectively. The hydrogen flow was 16 l/hr and the total pressure was 2000 psi. The product liquids were collected in duplicate at each temperature, stripped of unreacted isopropylamines, etc. and analyzed by chromatography and by wet chemical techniques. The results are summarized in Table III.

The data indicated that the combination of SURFONIC ® N-95 and isopropylamine gave poor yields of the desired "twin-tailed" tertiary amines (low tertiary amine content), although conversion to primary and secondary amines was high.

EXAMPLE II

Following the procedures of Example I, the 550-cc tubular reactor was charged with a copper chromite catalyst (Harshaw/Filtrol Cu-1184, T ⅛"). A mixture of SURFONIC® N-95 and methylamine were fed separately into the reactor at a rate of 0.22 and 0.02 lb/hr, respectively. The hydrogen flow rate was 16 1/hr and the pressure was 2000 psi. The product liquids are collected in duplicate at each reaction temperature, stripped of unreacted methylamines and lights, and analyzed by chromatography and wet chemical techniques. The results are summarized in the lower half of Table II.

The data indicated that Cu-1184 catalyst gives moderate yields of desired "twin-tailed" tertiary amines, and high yields of primary/secondary amines.

EXAMPLE III

Following the procedures of Example I, the 550-cc tubular reactor was charged with the nickel, copper and chromium-on-alumina catalyst (Ni-2728), but this time the liquid feed comprised SURFONIC® N-95 and dimethylamine. Here the feed rates were 0.22 and 0.10 lb/hr respectively. The hydrogen flow was 16 1/hr, the total pressure 2000 psi. The product liquids were collected in duplicate at each reaction temperature, stripped of lights and analyzed. The results are summarized in Table IV. Concentrations of desired tertiary amine comparable to those of primary/secondary amines, were achieved over the operating temperature range 190°–220° C.

EXAMPLE IV

Using the procedures, catalyst and reactor of Example I, a composite product mixture from Example I was fed to said reactor at a rate of 0.14 lb/hr in the presence of a hydrogen flow of 16 1/hr. Total pressure was held at 2000 psi. The product liquids were collected in duplicate at each reaction temperature, stripped of unreacted or light amines, and analyzed by chromatography and wet chemical techniques. The composition of both the composite feed and the product fraction are summarized in Table V.

The data indicate that a second pass through the reactor at 200°–210° C. accomplished the following.
a. Further increased the proportion of "twin-tailed" tertiary amine.
b. Raised the conversion of unreacted SURFONIC® N-95.

EXAMPLE V

Using the procedures, catalyst and reactor of Example I, a combination of SURFONIC® N-95 and methylamine were fed separately at a rate of 0.11 and 0.02 lb/hr respectively. The hydrogen feed rate was maintained at 16 lb/hr, the total pressure 2000 psi. The product liquids were collected in duplicate at each reaction temperature, stripped and analyzed. The results are summarized in Table VI.

Improved yields of the desired tertiary amines were achieved at these lower feed rates in comparison with those given in Table I. There was no evidence of catalyst deactivation basis the data for the first and last runs, both made at 190° C. and no evidence for product degradation.

TABLE I

TERTIARY AMINE SYNTHESIS FROM SURFONIC ® N-95 + METHYLAMINE

| EXAMPLE | CATALYST | OPERATING TEMP. (°C.) | Product Compsn. meq/g | | | gpc LOW MWT, AREA % | SAMPLE |
|---|---|---|---|---|---|---|---|
| | | | TERTIARY AMINE | PRI + SEC AMINE | UNREACTED OH | | |
| I | Ni-2728 | 190 | 0.49 | 0.67 | 0.32 | 0 | A |
| | | 200 | 0.44 | 0.51 | 0.24 | 0 | B |
| | | 210 | 0.40 | 0.58 | 0.19 | 0 | C |
| | | 220 | 0.36 | 0.79 | 0.08 | 0 | D |
| | | 235–240 | 0.10 | 0.84 | 0.07 | 5 | E |
| N-95 | | | | | 1.545 | | |

TABLE II

TERTIARY AMINE SYNTHESIS FROM SURFONIC ® N-95 + METHYLAMINE

| EXAMPLE | CATALYST | OPERATING TEMP. (°C.) | Product Compsn. meq/g | | | gpc LOW MWT |
|---|---|---|---|---|---|---|
| | | | TERTIARY AMINE | PRI + SEC AMINE | UNREACTED OH | |
| A | Ni-2715 | 210 | 0.03 | 0.76 | 0.02 | 9 |
| | | 220 | 0.02 | 0.49 | 0.06 | 7 |
| | | 230 | 0.02 | 0.54 | 0 | 7 |
| | | 240 | 0.01 | 0.44 | 0.12 | 7 |
| II | Cu-1184 | 200 | 0.21 | 0.93 | 0.33 | 0 |
| | | 210 | 0.35 | 0.80 | 0.23 | 0 |
| | | 220 | 0.38 | 0.86 | 0.20 | 0 |
| | | 230 | 0.07 | 0.09 | 1.31 | 0 |
| N-95 | | | | | 1.545 | |

TABLE III

TERTIARY AMINE SYNTHESIS FROM SURFONIC ® N-95 + ISOPROPYLAMINE

| EXAMPLE | CATALYST | OPERATING TEMP. (°C.) | Product Compsn. meq/g | | | gpc LOW MWT |
|---|---|---|---|---|---|---|
| | | | TERTIARY AMINE | PRI + SEC AMINE | UNREACTED OH | |
| B | Ni-2728 | 190 | 0.03 | 0.76 | 0.78 | 0 |
| | | 200 | 0.04 | 0.97 | 0.43 | 0 |

TABLE III-continued

TERTIARY AMINE SYNTHESIS FROM SURFONIC ® N-95 + ISOPROPYLAMINE

| EXAMPLE | CATALYST | OPERATING TEMP. (°C.) | TERTIARY AMINE | PRI + SEC AMINE | UNREACTED OH | gpc LOW MWT |
|---|---|---|---|---|---|---|
| | | 210 | 0.05 | 1.03 | 0.20 | 2 |
| | | 220 | 0.02 | 1.07 | 0.05 | 3 |

TABLE IV

TERTIARY AMINE SYNTHESIS FROM SURFONIC ® N-95 + DIMETHYLAMINE

| EXAMPLE | CATALYST | OPERATING TEMP. (°C.) | TERTIARY AMINE | PRI + SEC AMINE | UNREACTED OH |
|---|---|---|---|---|---|
| III | Ni-2728 | 190 | 0.69 | 0.61 | 0.16 |
| | | 210 | 0.63 | 0.66 | 0.09 |
| | | 220 | 0.63 | 0.65 | 0.10 |
| | | 240 | 0.50 | 0.64 | 0.13 |
| N-95 | | | | | 1.545 |

TABLE V

TERTIARY AMINE SYNTHESIS FROM EXAMPLE I PRODUCTS

| EXAMPLE | CATALYST | OPERATING TEMP. (°C.) | TERTIARY AMINE | PRI + SEC AMINE | UNREACTED OH | gpc LOW | SAMPLE |
|---|---|---|---|---|---|---|---|
| IV | Ni-2728 | 200 | 0.71 | 0.19 | 0.22 | 3 | A |
| | | 210 | 0.56 | 0.33 | 0.16 | 4 | B |
| | | 220 | 0.37 | 0.45 | 0.13 | 4 | C |

<sup>a</sup>From Example I

TABLE VI

TERTIARY AMINE FROM SURFONIC ® N-95 + METHYLAMINE

| EXAMPLE | CATALYST | OPERATING TEMP. (°C.) | TERTIARY AMINE | PRI + SEC AMINE | UNREACTED OH | gpc LOW |
|---|---|---|---|---|---|---|
| V | Ni-2728 | 190 | 0.41 | 0.85 | 0.21 | 0 |
| | | 200 | 0.53 | 0.76 | 0.04 | 0 |
| | | 210 | 0.50 | 0.60 | 0.18 | 0 |
| | | 190 | 0.41 | 0.86 | 0.15 | — |
| N-95 | | | | | 1.545 | |

EXAMPLE VI

Cloud points and viscosities of the "twin-tailed" tertiary amine products from Example 1 were measured on aqueous solutions of Samples C through E. The results are summarized in Table VII in comparison with the SURFONIC ® N-95 starting material. Of note are the pH-dependent cloud points and higher viscosity of the "twin tailed" tertiary amines compared to N-95. This behavior is indicative of the incorporated amine group and the amines' increased molecular weight.

TABLE VII

| SAMPLE | CLOUD POINT, 1% AQUEOUS | | | VISCOSITY @ 25° 20% AQUEOUS pH 9 |
|---|---|---|---|---|
| | AS IS (about pH 10) | pH 9 | pH 11 | |
| Product Ex. IC | 31° | >100° | 21° | 712 cps |
| Product Ex. ID | 34.5° | >100° | 29° | 642 cps |
| Product Ex. IE | 31° | >100° | 11.5° | 690 cps |
| SURFONIC ® N-95 | 53° | 54° | | 154 cps |

EXAMPLE VII

Cloud points and viscosities of the "twin-tailed" tertiary amine products from Example IV were measured on aqueous solutions of Samples A and B. The results are summarized in Table VIII. The improved surfactant properties of these twice-through products, in comparison with data both for the starting SURFONIC®-95 material, and for the products from Example I, Sample C, include:
A) Lower cloud points
B) Higher viscosities at pH 7

TABLE VIII

| SAMPLE | Cloud Point pH 11 | VISCOSITY, 20% AQUEOUS | |
|---|---|---|---|
| | | pH 7 | pH 10 |
| Product Ex. IVA | 6° | 185 cps | 258 cps |
| Product Ex. IVB | 9° | 146 cps | 318 cps |
| Product Ex. IC | 15.5° | 115 cps | 587 cps |

EXAMPLE VIII

Using the procedures, catalyst and reactor of Example I, the combination of SURFONIC® N-95 and methylamine were fed separately at rates of 0.11 lb/hr. and 0.05 lb/hr. respectively. Again the product liquids were collected in duplicate and each reaction temperature, stripped and analyzed. The results are summarized in Table IX.

TABLE IX

TERTIARY AMINE SYNTHESIS FROM SURFONIC ® N-95 + METHYLAMINE

| EXAMPLE | CATALYST | OPERATING TEMP. (°C.) | Product Compsn. Meq/g ||| 
| | | | TERTIARY AMINE | PRI + SEC AMINE | UNREACTED HYDROXYL |
| --- | --- | --- | --- | --- | --- |
| VIII | Ni-2728 | 190 | 0.13 | 1.20 | |
| | | 200 | 0.60 | 0.71 | 0.17 |
| | | 210 | 0.58 | 0.73 | 0.13 |
| N-95 | | | | | 1.545 |

EXAMPLE IX

Following the procedures of Example I, the 550 cc tubular reactor was again filled with the nickel, copper and chromium-on-alumina catalyst (Ni-2728 E 1/32"), but this time the liquid feed comprised SURFONIC® N-40 and methylamine. Here the feed rates were 0.11 and Ca 0.02 lb/hr., respectively. The hydrogen flow was 16 lb/hr. and the total pressure 2000 psi. The product liquids were collected in duplicate at each operating temperatures, stripped of unreacted methylamine, etc. and analyzed. The results are summarized in Table X.

TABLE X

TERTIARY AMINE SYNTHESIS FROM SURFONIC ® N-40 + METHYLAMINE

| EXAMPLE | CATALYST | OPERATING TEMP. (°C.) | Product Compsn. Meq/g ||| 
| | | | TERTIARY AMINE | PRI + SEC AMINE | UNREACTED HYDROXYL |
| --- | --- | --- | --- | --- | --- |
| IX | Ni-2728 | 190 | 0.73 | 1.07 | 0.37 |
| | | 200 | 0.83 | 1.03 | 0.12 |
| | | 210 | 0.73 | 1.00 | 0.17 |

EXAMPLE X

Using the procedures of Example IV, a composite product mixture from Ex. V was fed to the reactor and worked up. Analyses are summarized in Table XI.

TABLE XI

| OPERATING TEMP. (°C.) | TERTIARY AMINE meq/g | PRI + SEC AMINE | UNREACTED HYDROXYL | LOW MOL. WT. gpc. area % |
| --- | --- | --- | --- | --- |
| 190° | 0.59 | 0.42 | 0.07 | 2 |
| 190° | 0.59 | 0.42 | 0.07 | 2 |
| 200° | 0.56 | 0.43 | 0.06 | 2 |

The proportion of twin-tailed polyether amine in the products (tertiary amine in the products (tertiary amine content) increased substantially over the first pass (Ex. V), as did total conversion.

EXAMPLE XI

Surface tension measurements were carried out at 25° C. on two polyether amines as well as their precursor SURFONIC N-95 concentration was 0.10% (Table XII). These measurements demonstrate the high surface activity of methylaminated polyether surfactants.

TABLE XII

| SAMPLE | pH | SURFACE TENSION, DYNES/cm. |
| --- | --- | --- |
| Ex IX, 210° | 7.0 | 31.3 |
| | 9.0 | 30.4 |
| Ex X, 190° | 7.0 | 33.9 |
| | 9.0 | 30.7 |
| | 11.0 | 32.0 |
| SURFONIC N-95 | 9.0 | 30.4 |

What is claimed is:

1. A method for the synthesis of polyoxyalkylene tertiary amines having two moles of alkoxylated alkylphenol bonded to each tertiary nitrogen function which comprises:

alkylating a mole of methylamine with two moles of alkoxylated alkylphenol over a catalyst consisting essentially of;
5 to 70% nickel;
1 to 20% copper;
0.1 to 10% chromium; and
0.1 to 10% molybdenum on an alumina support, at a temperature of 150° C. to 300° C. and a pressure of 100 to 5000 psi.

2. The method of claim 1 wherein the alkylphenol is ethoxylated nonylphenol.

* * * * *